(12) United States Patent
Golebiowski et al.

(10) Patent No.: US 6,291,709 B1
(45) Date of Patent: Sep. 18, 2001

(54) SOLID SUPPORTED SYNTHESIS OF HYDROXAMIC ACIDS

(75) Inventors: Adam Golebiowski; Sean Rees Klopfenstein, both of Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/582,975
(22) PCT Filed: Dec. 28, 1998
(86) PCT No.: PCT/IB98/02117
   § 371 Date: Jul. 7, 2000
   § 102(e) Date: Jul. 7, 2000
(87) PCT Pub. No.: WO99/35126
   PCT Pub. Date: Jul. 15, 1999
(51) Int. Cl.$^7$ ................................................ C07C 259/04
(52) U.S. Cl. ............................................ 562/621; 562/622
(58) Field of Search ..................... 562/621, 622

(56) References Cited

FOREIGN PATENT DOCUMENTS

WO9626223 * 8/1996 (WO) .
WO98/18754 * 5/1998 (WO) .

OTHER PUBLICATIONS

Golebiowski et al, Solid Supported Synthseis of Hydroxamic Acids, accepted: Mar. 4, 1998, Tetrahedron Letters 39 (1998), pp. 3397–3400.*

* cited by examiner

*Primary Examiner*—Gary Geist
*Assistant Examiner*—Hector M Reyes
(74) *Attorney, Agent, or Firm*—David V. Upite; Carl J. Roof

(57) ABSTRACT

The subject invention involves processes for making hydroxamic acid compounds using a solid-support resin having an oxime moiety as the linking moiety of the resin, comprising the steps of (a) treating the resin with a carboxylic acid compound, such that it is attached to the resin by a condensation reaction between the oxime and carboxyl moieties; (b) optionally modifying the side chain; (c) cleaving a product from the resin by treating with O-tert-butyldimethylsilylhydroxylamine; (d) optionally modifying the side chain; and (e) optionally treating the resulting O-TBS-protected material with acid to produce an unprotected hydroxamic acid compound.

16 Claims, No Drawings

SOLID SUPPORTED SYNTHESIS OF HYDROXAMIC ACIDS

TECHNICAL FIELD

The subject invention relates to methods for synthesizing hydroxamic acid compounds using a solid-support resin to facilitate purification of intermediates.

BACKGROUND OF THE INVENTION

Hydroxamic acids are an important class of organic molecules playing a key role in many biologically relevant interactions. Inhibition of matrix metalloproteinases (MMPs) (see Greenwald, R. A.; Golub, L. M., Eds.; *Inhibitioin of Matrix Metalloproteinases: Therapeutical Potential;* New York Academy of Sciences, vol. 732 (1994), and Rockwell, A.; Melden, M.; Copeland, R. A.; Hardman, K.; Decicco, C. P.; DeGrado, W. F.; *J. Am. Chem. Soc.,* vol. 118 (1996), p. 10337 and references therein) or a unique deacetylase of lipid A biosynthesis (see Onishi, R. H.; Pelak, B. A.; Gerckens, L. S.; Silver, L. L.; Kahan, F. M.; Chen, M-H.; Patchett, A. A.; Galloway, S. M.; Hyland, S. A.; Anderson, M. S.; Raetz C. R. H.; *Science,* vol. 274 (1996), p. 980) testify to the significance of this class of compounds.

Synthesis on solid support is a crucial technology for combinatorial chemistry efforts. It allows for easy automation of processes and convenient handling of polar molecules throughout the synthetic protocol. It also provides a reliable method for the preparation of mixtures of compounds (split-mix synthesis). The solid supported synthesis of hydroxamic acids, based on Wang, Sasrin, or the 2-chlorotrityl O-hydroxylamine bound resin have recently been reported. (See Richter, L. S.; Desai, M. C.; *Tetrahedron Lett.,* vol. 38 (1997), p. 321; Gordeev, M. F.; Hui, H. C.; Gordon, E. M.; Patel, D. V.; *Tetrahedron Lett.,* vol. 38 (1997), p. 1729; Mellor, S. L.; McGuire, C.; Chan, W. C.; *Tetrahedron Lett.,* vol. 38 (1997), p. 3311; and Bauer, U.; Ho, W-B.; Koskinen, A. M. P.; *Tetrahedron Lett.,* vol. 38 (1997), p. 7233.) Another alternative synthetic approach, based on resin N-linked hydroxylamine has been reported. (See Ngu, K.; Patel, D. V.; *J. Org. Chem.,* vol. 62 (1997), p. 7088.)

We have found two major limitations of the reported methods for making hydroxamic acids using solid-support resins. First, during side chain modifications we sometimes observed undesired functionalization of the nitrogen which ultimately is part of the hydroxylamino moiety of the hydroxamic acid: Resin-ONHCOR. Second, none of the above reported methods allows application of acid labile protecting groups (e.g. Boc) during side-chain synthesis.

SUMMARY OF THE INVENTION

The subject invention involves processes for making hydroxamic acid compounds: RC(O)NHOH, using a solid-support resin having an oxime moiety: Resin:C=N—OH, as the linking moiety of the resin, comprising the following steps:

(a) treating the resin with a carboxylic acid compound: R'C(O)OH, having a carboxyl moiety: C(O)OH, and a side chain moiety: R', whereby the carboxylic acid compound becomes attached to the resin due to a condensation reaction between the oxime and carboxyl moieties;

(b) optionally modifying the side chain R' to produce side chain R of the target hydroxamic acid compound or an intermediate side chain R", through one or more reaction and purification procedures, whereby a resin, linking, and attached moiety has the structure:
Resin:C=NOC(O)R' or Resin:C=NOC(O)R or Resin:C=NOC(O))R";

(c) cleaving a product from the resin by treating with O-tert-butyldimethylsilylhydroxylamine: TBSONH$_2$, to produce a TBS-protected hydroxamic acid compound: R'C(O)NHOTBS or RC(O)NHOTBS or R"C(O)NHOTBS;

(d) optionally modifying the side chain R' or R" to produce the side chain R of the target hydroxamic acid compound, whereby RC(O)NHOTBS is produced; and (e) optionally treating the RC(O)NHOTBS with acid to produce an unprotected hydroxamic acid compound: RC(O)NHOH.

DETAILED DESCRIPTION OF THE INVENTION

The subject invention involves processes for making hydroxamic acid compounds:

$$RC(O)NHOH \quad (1)$$

Many hydroxamic acids are known. In structure (1), R can be virtually any organic radical. It is limited only by stability and solubility factors during processing and as part of the final product.

The subject invention processes use a solid-support resin having an oxime moiety as the linking moiety of the resin. A preferred resin is an oxime (Kaiser) resin available commercially from Novabiochem, San Diego, Calif., having the structure:

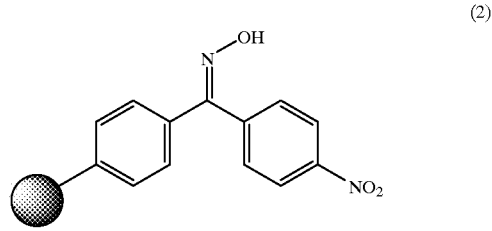

(2)

where ◯ is the resin backbone.

The first step of the subject invention processes involves treating the resin with a carboxylic acid compound:

$$R'C(O)OH \quad (3)$$

Many carboxylic acids are known. R' can be virtually any organic radical that provides a stable and soluble compound (3), and will not react preferentially (to the acid moiety) with the oxime moiety of the resin. R' can be the same or different from R. The carboxylic acid becomes attached to the resin by a simple condensation reaction between the carboxyl moiety of the carboxylic acid and the oxime moiety of the resin. Preferably the reaction is carried out with the resin suspended in dichloromethane (DCM) in the presence of one equivalent of 1,3-diisopropylcarbodiimide (DIC) and a catalytic amount of 4-dimethylaminopyridine (DMAP).

If R' is different from the desired R of the hydroxamic acid being produced, one or more reaction and purification procedures can be used to modify the structure of the side chain R'. This second step is optional since R' and R may be the same moiety, or no modification of R' may be desired at this stage of the process. However, this second step is preferably used, since the ease of modifying R' during this step is one of the primary advantages of the subject processes.

Linkage of the material undergoing modification to the solid-support resin provides the advantage of easy purification of intermediates by simply washing excess reagents and impurities from the resin-bound materials using appropriate solvents. An advantage of the subject invention process is that the linkage of the product to the oxime resin is typically both acid and base stable to a sufficient extent that a wide variety of reactions can be utilized in modifying the side chain of the product. This includes the use of both acid and base labile protecting groups during these reaction and purification steps.

Ultimately these reaction and purification steps provide a resin-bound material having the structure:

Resin:C=NOC(O)R*      (4)

where R* is R or R' or R". A product is cleaved from the resin in a third step by treating structure (4) with O-tert-butyldimethylsilylhydroxylamine:

TBSONH$_2$ where TBS is tert-butyldimethylsilyl, producing an O-tert-butyldimethylsilyl-protected hydroxamic acid compound:

R*C(O)NHOTBS      (5)

The O-TBS-protected product (5) may be useful in its own right, if further modifications of the material are desired to be made with the O-protecting group in place. If R* is R' or R", it is modified in an optional fourth step through one or more reaction and purification procedures to produce side chain R of the target hydroxamic acid compound:

RC(O)NHOTBS      (6)

This step is optional since it is not needed if R* is R.

The corresponding unprotected hydroxamic acid compound is produced in a fifth step by treating structure (6) with acid, producing the target compound:

RC(O)NHOH      (1)

This step is optional, because it may be desirable to retain the hydroxamic acid compound produced in its O-TBS-protected state.

While inorganic acids such as HCl or HBr can be used in this fifth step to produce the hydroxamic acid, the use of a volatile organic acid, such as trifluoroacetic acid (TFA), is highly preferred. Both TBSONH$_2$ and an acid such as TFA are generally more volatile than the unprotected hydroxamic acid product, so that excess amounts of them are readily separated from the unprotected hydroxamic acid compound by evaporation.

The subject invention processes provide easy purification of intermediates which are bonded to the resin, and easy purification of the final product due to the volatility of the reagents used. This makes the processes amenable to automation. They are readily used for providing mixed-compound or isolated-compound combinatorial libraries of compounds. The subject processes also minimize undesired functionalization of the nitrogen which ultimately is part of the hydroxylamino moiety of the hydroxamic acid produced.

A preferred exemplary synthetic route, which is outlined in Scheme 1, utilizes oxime (Kaiser) resin (1) which is reacted with carboxylic acid to produce esters (2). After side chain modification, the product is cleaved as an O-protected hydroxamic acid (3), using O-tert-butyldimethylsilylhydroxylamine. (At this stage the crude product can be purified by silica gel chromatography.) Finally, the silyl group is removed with trifluoroacetic acid at room temperature to afford pure hydroxamic acid (4)

Scheme 1

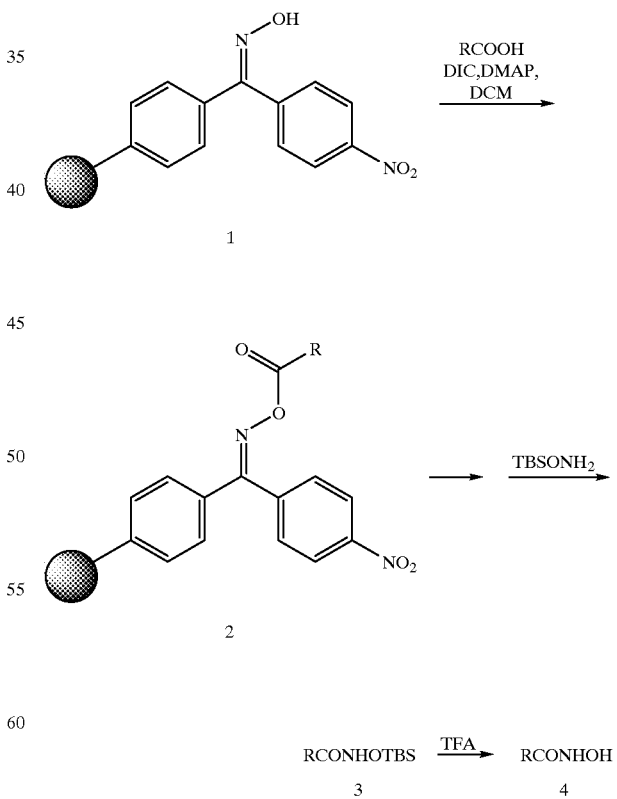

A small exemplary set of hydroxamic acids prepared by the process of Scheme 1 is shown in Table 1:

TABLE 1

| Example | Acid | Hydroxamic acid (4) | Yield | Purity |
|---|---|---|---|---|
| A | 2-furoic acid | 2-furoyl hydroxamic acid | 72 | 95 |
| B | 4-methoxybenzoic acid | 4-methoxybenzoyl hydroxamic acid | 36 | 95 |
| C | 4-(methylthio)benzoic acid | 4-(methylthio)benzoyl hydroxamic acid | 34 | 95 |
| D | 1-naphthoic acid | 1-naphthoyl hydroxamic acid | 27 | 90 |
| E | 1-naphthaleneacetic acid | 1-naphthaleneacetyl hydroxamic acid | 89 | 90 |
| F | 2-phenylpropanoic acid | 2-phenylpropanoyl hydroxamic acid | 74 | 85 |
| G | hexanoic acid | hexanoyl hydroxamic acid | 68 | 90 |

The following description details the making of 2-furoic hydroxamate, Example A in Table 1. Oxime resin (1.0 g, 1.17 mmol/g, 1.17 mmol; Novabiochem, product number 01-64-0022) is rinsed several times with dichloromethane (DCM). 2-Furoic acid (5 eq, 655 mg, 5.85 mmol) in DCM (12 mL) is added, followed by 1,3-diisopropylcarbodiimide (DIC; 737 mg, 5.85 mmol) and a catalytic amount of 4-dimethylaminopyridine (DMAP, 5 mg). The reaction mixture is shaken for 17 hours and the resin is filtered and washed (DCM, 2-propanol, dimethylformamide (DMF)). Alternate washing with DCM and 2-propanol is repeated several times, and finally the resin is dried under vacuum for several hours at room temperature. The resin is swelled in 1,2-dichloroethane (DCE, 10 mL). TBSONH$_2$ (107 mg, 0.730 mmol, 5 eq) is added and the reaction mixture is refluxed for 20 h (ca. 90° C.). The resin is filtered and washed (DCM); the filtrate is collected and evaporated. The oily residue is vacuum dried and co-evaporated with chloroform several times to give 198 mg of oily product. This residue is dissolved in TFA:water (95:5; v:v) and stirred for 16 h, then evaporated to yield a yellowish, waxy solid, 131 mg (95% purity).

To demonstrate the possibility of using acid labile protecting groups, N-tosyl-proline hydroxamic acid (8) is prepared according to Scheme 2 and the following described procedure:

Scheme 2

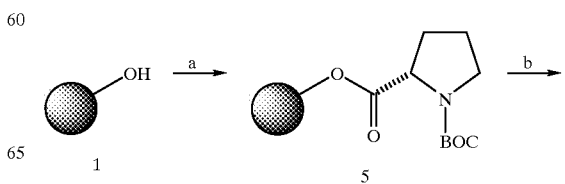

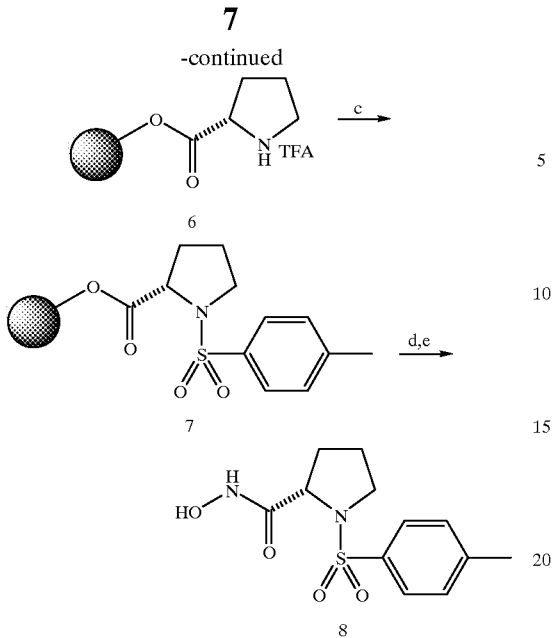

Reagents: a) Boc-Pro-OH, DIC, DMAP, DCM; b) 25% TFA/DCM; c) TsCl, DIPEA, DCM; d) TBSONH$_2$, DCE; e) 95% TFA/H$_2$O.

Oxime resin (1.0 g, 1.17 mmol/g, 1.17 mmol; Novabiochem, product number 01-64-0022) is rinsed several times with DCM. Boc-proline (5 eq, 1.28 g, 5.85 mmol) in DCM (12 mL) is added, followed by DIC (737 mg, 5.85 mmol) and a catalytic amount of DMAP (5 mg). The reaction mixture is shaken for 17 hours, and the resin is filtered and washed (DCM, 2-propanol, DMF). Alternate washing with DCM and 2-propanol is repeated several times, and finally the resin is dried under vacuum for several hours at room temperature to give 1.188 g of Boc-proline loaded resin (yield 96.5%, new loading 0.78 mmol/g). The Boc-proline oxime resin ester (158 mg, 0.146 mmol) is treated with 25% TFA in DCM and shaken for 1 h. The resin is filtered and washed several times with DCM and 10% DIPEA/DCM. DCE and N,N-diisopropylethylamine (DIPEA) are added (2:1, total 5 mL), followed by tosyl chloride (TsCl, 140 mg, 0.730 mmol, 5 eq). The reaction mixture is shaken for 6 h, then filtered, washed (DCM, 2-propanol and again DCM several times) and vacuum dried (room temperature, 48 h). The resin is swelled in DCE (10 mL) and TBSONH$_2$ (0.107 mg, 0.730 mmol 5 eq) is added, and the reaction mixture is refluxed for 20 h (ca. 90° C.). The resin is filtered and washed (DCM); the filtrate is collected and evaporated. The oily residue is vacuum dried and co-evaporated with chloroform several times to give 55.2 mg of oily product (95% yield). The oily product is dissolved in TFA:water (95:5; v:v) and stirred for 16 h, then evaporated to yield a yellowish, waxy solid.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A process for making a hydroxamic acid compound using a solid-support resin having an oxime moiety as the linking moiety of the resin, comprising the following steps:

(a) treating the resin with a carboxylic acid compound having a carboxyl moiety and a side chain moiety, whereby the resin is loaded by attachment of the carboxylic acid compound to the resin due to a condensation reaction between the oxime and carboxyl moieties;

(b) optionally, while on the loaded resin, modifying the side chain from the carboxylic acid compound through one or more reaction and purification procedures;

(c) cleaving a product from the loaded resin of step (b) by treating with O-tert-butyldimethylsilylhydroxylamine: to produce an O-TBS-protected hydroxamic acid compound;

(d) optionally modifying the side chain from step (b) through one or more reaction and purification procedures; and (e) optionally treating the O-TBS-protected hydroxamic acid compound from step (d) with acid to produce an unprotected hydroxamic acid compound.

2. The process of claim 1 wherein step (b) is not optional.

3. The process of claim 1 wherein step (e) is not optional, and the acid used in step (e) is a volatile acid.

4. The process of claim 2 wherein step (b) comprises a reaction where the side chain has an acid-labile or base-labile protecting group.

5. The process of claim 4 wherein step (b) comprises a reaction where the side chain has an acid-labile protecting group.

6. The process of claim 4 wherein step (b) comprises a reaction where the side chain has a base-labile protecting group.

7. The process of claim 4 wherein step (e) is not optional, and the acid used in step (e) is a volatile organic acid.

8. The process of claim 7 wherein the acid used in step (e) is trifluoroacetic acid.

9. The process of claim 1 wherein the side chain from the carboxylic acid compound is modified producing the side chain of the hydroxamic acid compound in step (b), and step (d) is not used, so that in step (e), the O-TBS-protected hydroxamic acid compound from step (c) is treated.

10. The process of claim 9 wherein step (b) is not optional, and step (b) comprises a reaction where the side chain has an acid-labile or base-labile protecting group.

11. The process of claim 9 wherein step (e) is not optional, and the acid used in step (e) is a volatile organic acid.

12. The process of claim 10 wherein step (e) is not optional, and the acid used in step (e) is a volatile organic acid.

13. The process of claim 12 wherein the acid used in step (e) is trifluoroacetic acid.

14. The process of claim 1 wherein the resin has the structure:

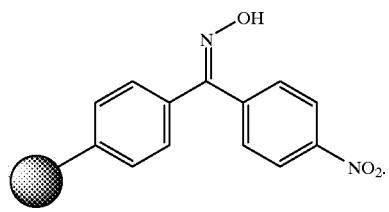
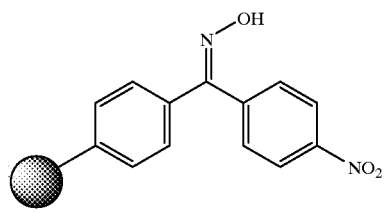
15. The process of claim 1 wherein the process is used to make a combinatorial library of compounds.
16. The process of claim 11 wherein the resin has the structure:
and the process is used to make a combinatorial library of compounds.
* * * * *